US009474497B2

(12) United States Patent
Kopylov (10) Patent No.: US 9,474,497 B2
(45) Date of Patent: Oct. 25, 2016

(54) METHOD AND SYSTEM FOR GENERATING PRE-SCALED IMAGES FOR A SERIES OF MAMMOGRAPHY IMAGES

(71) Applicant: Viktor Kopylov, Kitchener (CA)

(72) Inventor: Viktor Kopylov, Kitchener (CA)

(73) Assignee: AGFA HEALTHCARE, Mississauga (CA)

( * ) Notice: Subject to any disclaimer, the term of this patent is extended or adjusted under 35 U.S.C. 154(b) by 70 days.

(21) Appl. No.: 14/155,851

(22) Filed: Jan. 15, 2014

(65) Prior Publication Data

US 2015/0199790 A1 Jul. 16, 2015

(51) Int. Cl.
| | |
|---|---|
| *G06T 3/40* | (2006.01) |
| *A61B 6/00* | (2006.01) |
| *A61B 6/02* | (2006.01) |
| *A61B 6/03* | (2006.01) |

(52) U.S. Cl.
CPC ............... *A61B 6/502* (2013.01); *A61B 6/463* (2013.01); *A61B 6/466* (2013.01); *A61B 6/5235* (2013.01); *G06T 3/40* (2013.01); *A61B 6/025* (2013.01); *A61B 6/032* (2013.01); *A61B 6/486* (2013.01); *G06T 2207/10016* (2013.01); *G06T 2207/10116* (2013.01); *G06T 2207/30068* (2013.01)

(58) Field of Classification Search
CPC ........... G06T 3/40; G06T 2207/30068; A61B 6/5235
See application file for complete search history.

(56) References Cited

U.S. PATENT DOCUMENTS

| | | | |
|---|---|---|---|
| 7,129,961 B1 * | 10/2006 | Samra | G06T 11/60 345/620 |
| 7,142,633 B2 | 11/2006 | Eberhard et al. | |
| 7,599,542 B2 | 10/2009 | Brockway et al. | |
| 7,885,443 B2 | 2/2011 | Zingaretti et al. | |
| 7,992,100 B2 | 8/2011 | Lundstrom et al. | |
| 8,044,972 B2 | 10/2011 | Hall et al. | |
| 8,051,386 B2 | 11/2011 | Rosander et al. | |
| 8,923,594 B2 | 12/2014 | Wehnes et al. | |
| 2006/0098855 A1 | 5/2006 | Gkanatsios et al. | |
| 2011/0109650 A1 | 5/2011 | Kreeger et al. | |
| 2011/0216949 A1 | 9/2011 | Yang | |

FOREIGN PATENT DOCUMENTS

WO    2011044295 A3    4/2011

OTHER PUBLICATIONS

International Search Report and Written Opinion, International Application No. CA2015/000021 dated Apr. 30, 2015.

* cited by examiner

*Primary Examiner* — Jeffery A Brier
(74) *Attorney, Agent, or Firm* — Bereskin & Parr LLP; Isis E. Caulder (57) ABSTRACT

A computer implemented method for generating a pre-scaled image for at least one mammography image of a series, the series containing a plurality of mammography images, each mammography image displaying a breast having tissue points, the method comprising: obtaining an overview breast window, wherein the overview breast window encloses all tissue points; and, rendering the pre-scaled image based on the overview breast window. In some embodiments, the overview image, the overview breast window, or both may be stored in the database memory. In some embodiments, the overview breast window may be stored as the image breast window for each image of the series.

16 Claims, 11 Drawing Sheets

METHOD AND SYSTEM FOR GENERATING PRE-SCALED IMAGES FOR A SERIES OF MAMMOGRAPHY IMAGES

FIELD

The embodiments described herein relate to a system and method for image analysis and more particularly a system and method for generating a pre-scaled image for at least one mammography image of an image series.

BACKGROUND

Medical personnel (e.g. radiologists) examine mammography images to diagnose various abnormalities in a breast. When examining these images within a viewing area on a mammography system, medical personnel desire to review the mammography image displaying a breast (i.e. the breast image), with little regard to any of the background. Also, as medical personnel are primarily interested in the breast area, it is highly desirable to extract this breast area and display it at an optimal and consistent scale across all displayed images. That is, medical personnel seek mammography systems that facilitate quickly generated diagnostic reviews of mammography images, and allow for convenient navigation and review between views of a medical imaging data set while maintaining the same presentation state, including for example the scale factor, across all of the images in the views.

Medical personnel have typically used the zooming and panning functionality of a mammography system. Specifically, once the user has positioned the mouse on a part of the mammography image that the user wants to focus on, using the zooming and panning functionality of the mammography system. Doing so for each successive image is time-consuming and inconvenient.

More efficient diagnostic review of mammography images has been facilitated through the use of a breast window. A breast window for a breast image is considered to be the smallest region that encloses all of the tissue points of a breast shown on mammography image. A breast window may be characterized by the size of the region as well as the location of the region within the mammography image. The mammography system may also define a breast window that contains an optimal part of a breast image and displays it optimally scaled (herein referred to as a "pre-scaled image") such that the defined breast window fills the entirety of the viewing area of the mammography system. Use of a breast window can eliminate the time-consuming and inconvenient process of manual adjustment which may require re-iterative zooming and panning for each image within a plurality of mammography images.

Traditionally, older modalities, such as x-ray or magnetic resonance tomography, have produced individual mammography images that are two-dimensional images. A plurality of mammography images from a single modality may be considered to be an image series (also referred to as a series of mammography images).

Newer modalities, such as x-ray tomosynthesis or computed tomography imaging modalities, produce "volume-based" mammography images, which for example, may comprise a plurality of two-dimensional images stacked in series. Volume-based images are generated by first, processing traditional two-dimensional images to render additional images which may show the breast at different angles. These images are then used to generate the volume-based images in an image series. Medical personnel may view all images of an image series together by generating an overview image, or by obtaining an overview image from a modality. Wherein the overview image shows all or a subset of, tissue points from each image in the image series on a single two-dimensional image.

Current solutions that utilize breast windows typically identify a region of interest within each mammography image by processing each image. Next, the best scaling factor is determined and then mammography image is displayed using an individually calculated "scale to fit" factor. The result is that medical personnel cannot rely on the visual appearance of an anatomical element within a mammography image. To overcome this uncertainty it is necessary for the user to use manual display functionality through the graphical user interface to assess size characteristics of the anatomical element. This process is even more disruptive to the workflow than the system adjustments (i.e. zoom and pan) which the breast window-based solutions were aimed to replace. To address this, some mammography systems process the breast window for each image to be displayed to determine the common scale factor. The common scale factor then applied to all images in the series. This approach eliminates the need for manual zoom and pan, but requires time to process each image and determine the corresponding breast window, which impacts procedural efficiency of breast screening by mammography.

While current solutions are effective when applied to conventional mammogram image studies where a study is composed of individual mammography images. Current solutions are far less desirable for use with a volume based series of mammography images. Every time a new mammography image is added or viewed a new breast window needs to be calculated and there is an inherent delay before the optimal view can be displayed.

Overall the processing requirements behind the calculation of breast windows for each image in an image series creates significant processing and performance demands over the course of reviewing an image series. As a result, the cumulative time in which medical personnel may wait for the processor to render pre-scaled images can be very time-consuming and inconvenient, particularly in regards to mammography screening workflow. As new modalities continue to generate larger image data, the greater processing demands may decrease reliability and increase hardware infrastructure costs. There is a need for a mammographic system that provides more efficient review and navigation of an image series.

SUMMARY

In accordance with an aspect of an embodiment of the invention, there is provided a method for generating a pre-scaled image for at least one mammography image of a series, the series containing a plurality of mammography images, each mammography image displaying a breast having tissue points. The method comprising: obtaining an overview breast window, wherein the overview breast window encloses all tissue points; adjusting, if required, the overview breast window, for example in size, position, orientation or alignment, and storing it as an image breast window, applying the image breast window to apportion each image in the series, creating a breast window image; and rendering the pre-scaled image based on the breast window image for each image in the image series.

In accordance with an embodiment of the invention, there is provided a system for generating a pre-scaled image for at least one mammography image of a series, the series containing a plurality of mammography images, each mammography image displaying a breast having tissue points. The system comprising: a database memory for storing the overview breast window; and, a processor coupled to the database memory and configured to obtain an overview breast window, wherein the overview breast window encloses all tissue points, adjusting the overview breast window, for example in size, position, orientation or alignment, and storing the adjusted overview breast window as an image breast window, applying the image breast window to apportion each image in the series to create a breast window image, and rendering the pre-scaled image based on the breast window image.

Further aspects and advantages of the embodiments described herein will appear from the following description taken together with the accompanying drawings.

DRAWINGS

For a better understanding of the embodiments described herein and to show more clearly how they may be carried into effect, reference will now be made, by way of example only, to the accompanying drawings which show at least one exemplary embodiment, and in which.

The skilled person in the art will understand that the drawings, described below, are for illustration purposes only. The drawings are not intended to limit the scope of the applicants' teachings in any way. Also, it will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF VARIOUS EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein. Where considered appropriate, for simplicity and clarity of illustration, reference numerals may be repeated among the figures to indicate corresponding or analogous elements or steps.

The embodiments of the systems and methods described herein may be implemented in hardware or software, or a combination of both. However, preferably, these embodiments are implemented in computer programs executing on programmable computers each comprising at least one module component which comprises at least one processor (e.g. a microprocessor), a data storage system (including volatile and non-volatile memory and/or storage elements), at least one input device, and at least one output device. For example and without limitation, the programmable computers (referred to below as computing devices) may be a personal computer, laptop, personal data assistant, and cellular telephone, smart-phone device, tablet computer, and/or wireless device. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The subject system may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

Further, although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

Figure 1A:
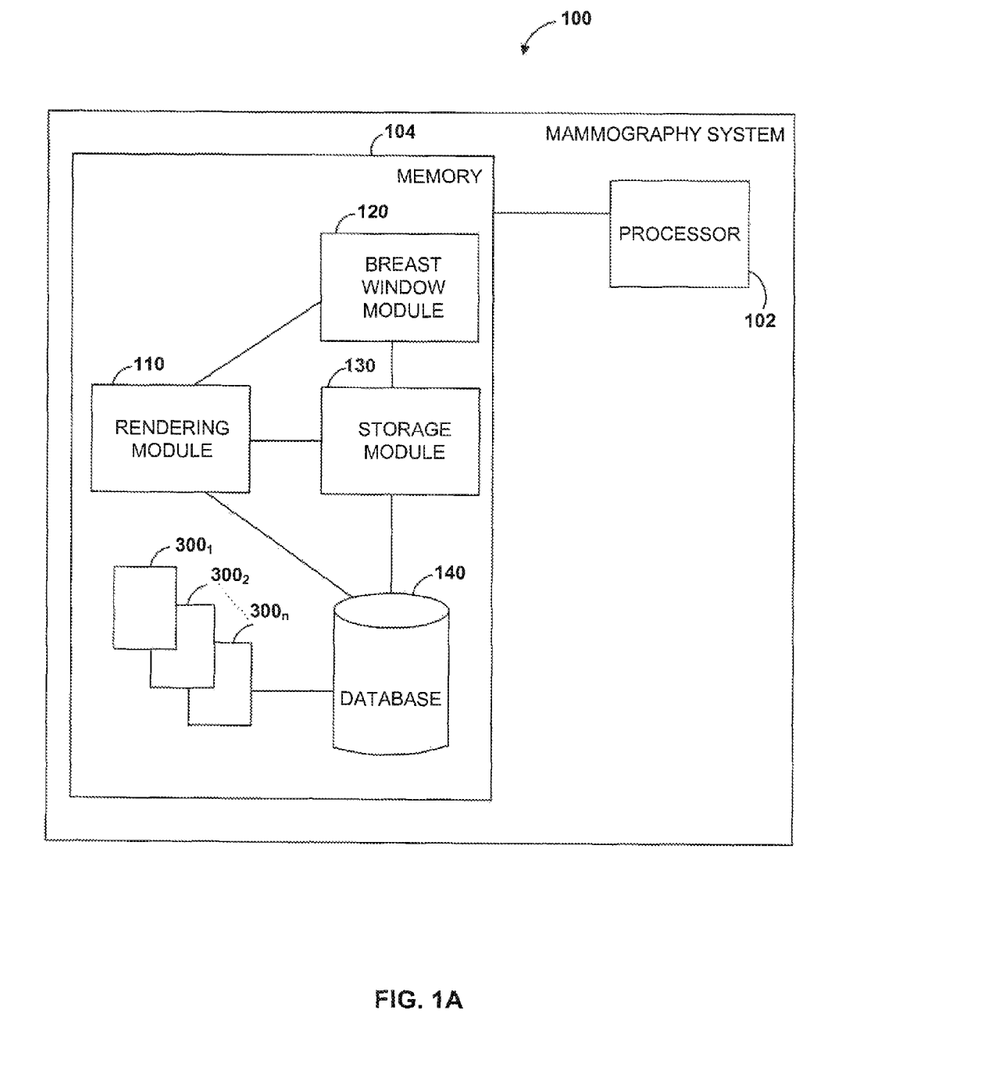
FIG. 1A is a block diagram of a mammography system.

Referring to FIG. 1A which illustrates an example embodiment of a mammography system 100. Mammography system 100 may contain a processor 102 that is operatively coupled to memory 104. Memory 104 may store a breast window module 120 for defining an overview breast window 380 or image breast window $385_n$ applied on a plurality of images $300_1$ to $300_n$ (where $300_1$ represents a first image and $300_n$ represents an $n^{th}$ image and $385_n$ represents the image breast window corresponding to the $n^{th}$ image), a rendering module 110 for rendering new volume based image series from an existing image series or a new overview image 350 from an existing image series (e.g. a pre-scaled image $395_n$ or an overview image 350 for a plurality of images $300_1$ to $300_n$) using an overview breast window 380 or image breast window $385_n$, and a storage module 130 for storing an overview breast window 380 or image breast window $385_n$ on a database 140. In some embodiments, the storage module 130 may also store other data such as for example, an overview image 350.

Images $300_1$ to $300_n$ stored on image database 140 may be mammography images. In various embodiments, images $300_1$ to $300_n$ may be images obtained directly from a modality, overview images, or rendered images (e.g. multi-planar reformatted images), including volume-based images.

Figure 1B:
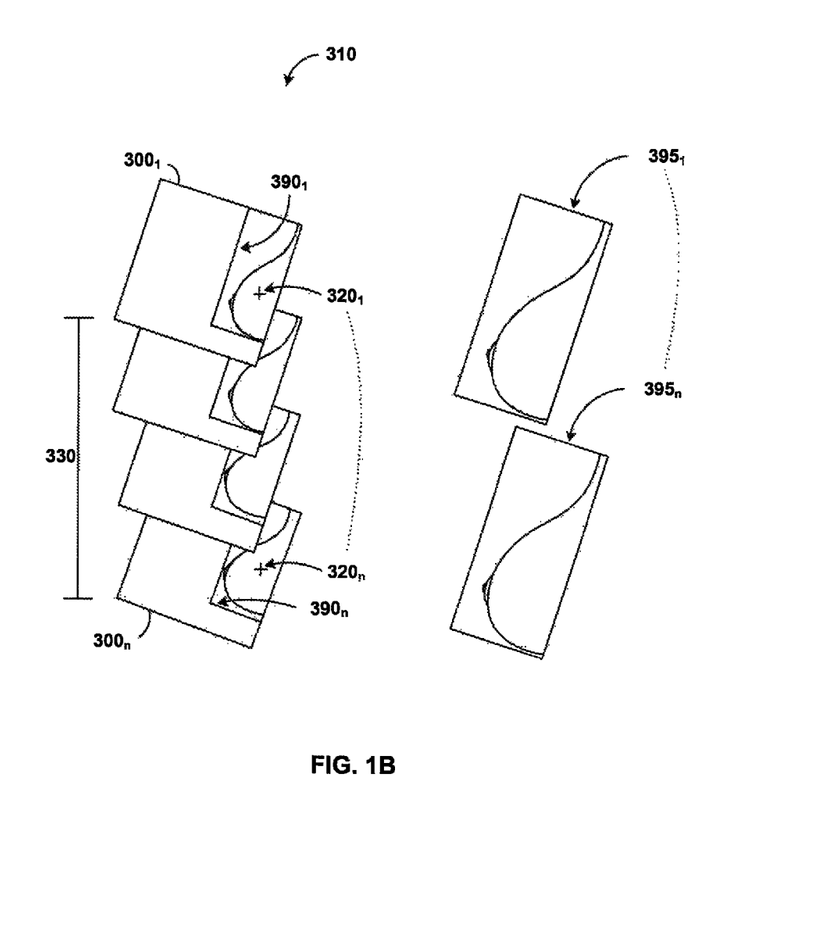
FIG. 1B is a schematic illustration of an image breast window and depth for a given plurality of mammography images.

Referring now to FIG. 1B, therein illustrated is a schematic diagram of the volume-based pre-scaled images $395_1$ to $395_n$ for an image series 310 which contains a plurality of images $300_1$ to $300_n$ (where $300_1$ represents a first image and $300_n$ represents an $n^{th}$ image, and $395_1$ represents a pre-scaled image for the first mammography image $300_1$, and $395_n$ represents a pre-scaled image for the $n^{th}$ mammography image $300_n$).

A breast window image $390_{1 \ldots n}$ is rendered for each corresponding image $300_{1 \ldots n}$ of the image series 310. The volume-based image has a depth 330, which is the distance between the first image $300_1$ and the last image $300_n$ when the images are in spatial order.

Images $300_1$ to $300_n$ may be processed to generate another plurality of images $300_1$ to $300_m$ showing, for example, the breast at different angles with different slice thicknesses, etc.

Figure 1C:
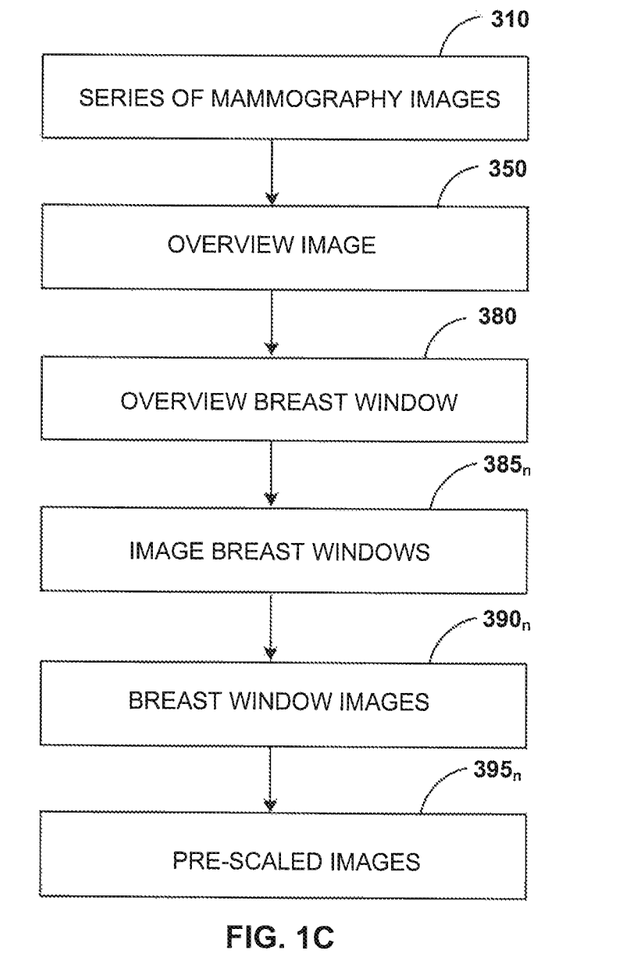
FIG. 1C is a data flow diagram illustrating the process that is used for generating a pre-scaled image for at least one mammography image of a series within the mammography system of FIG. 1A.

Referring now to FIG. 10, therein illustrated is the general flow of data used for generating a pre-scaled image $395_{1 \ldots n}$ for at least one mammography image, $300_{1 \ldots n}$, of an image series 310.

Images series 310 may be obtained directly from a modality or generated from an existing series. Overview image 350 is generated from or obtained for the image series 310, and represents all or a subset of, images contained in the series.

An overview breast window 380 is defined for the overview image 350 as a portion of the overview image, for example a rectangular shape, that contains all, or a subset of, the projected tissue points inside the overview image 350.

The overview breast window 380 is then used to create the image breast windows $385_n$. This process may include adjustments, for example, for differences in size, position, alignment or orientation, for each image represented in the overview image.

Each breast window image $390_n$ is the image resulting from cropping each image represented in the overview image by the boundary defined by the image breast window $385_n$.

The breast window images $390_{1 \ldots n}$ are then used to generate pre-scaled images $395_{1 \ldots n}$ for each image, $300_{1 \ldots n}$, in image series 310. The pre-scaled image is automatically adjusted, for example, by scaling, panning, flipping, or rotating, to consistently render each image in an image series.

Referring back now to FIGS. 1A, 1B, 10, and FIGS. 3B to 3E, breast window module 120 may be configured to receive notifications that one of a plurality of images, $300_{1 \ldots n}$, is ready for breast window definition. For each image $300_{1 \ldots n}$ used to create the overview image 350, the system generates a corresponding image breast windows $385_{1 \ldots n}$, breast window images $390_{1 \ldots n}$, and pre-scaled images $395_{1 \ldots n}$.

The breast window module 120 may define an overview breast window 380 around an overview image 350. An overview breast window 380 is considered to be the smallest region (for example, a rectangle in one example embodiment) that encloses all, or a subset of, the tissue points of a breast displayed on a mammography image. The breast window module 120 may send notifications after it has defined an overview breast window 380 or image breast window $385_n$. As shown, an overview breast window may be defined by the size of the region enclosing all or some of the tissue points or by the location coordinates of the region within the image.

Rendering module 110 may be configured to receive notifications to render a pre-scaled image $395_n$. Once an overview breast window 380 (FIG. 1C and FIG. 3B) and image breast window $385_n$ are defined by breast window module 120 for each image in the image series 310, the rendering module 110 may render a pre-scaled image $395_n$ from the breast window image $390_n$ for each image in the image series 310. The pre-scaled image 395$_n$ is rendered then mapped to the entirety of the viewing area in a consistent manner across all the viewing areas. In some embodiments, the system may elect to render a subset of pre-scaled images.

Figure 3A:
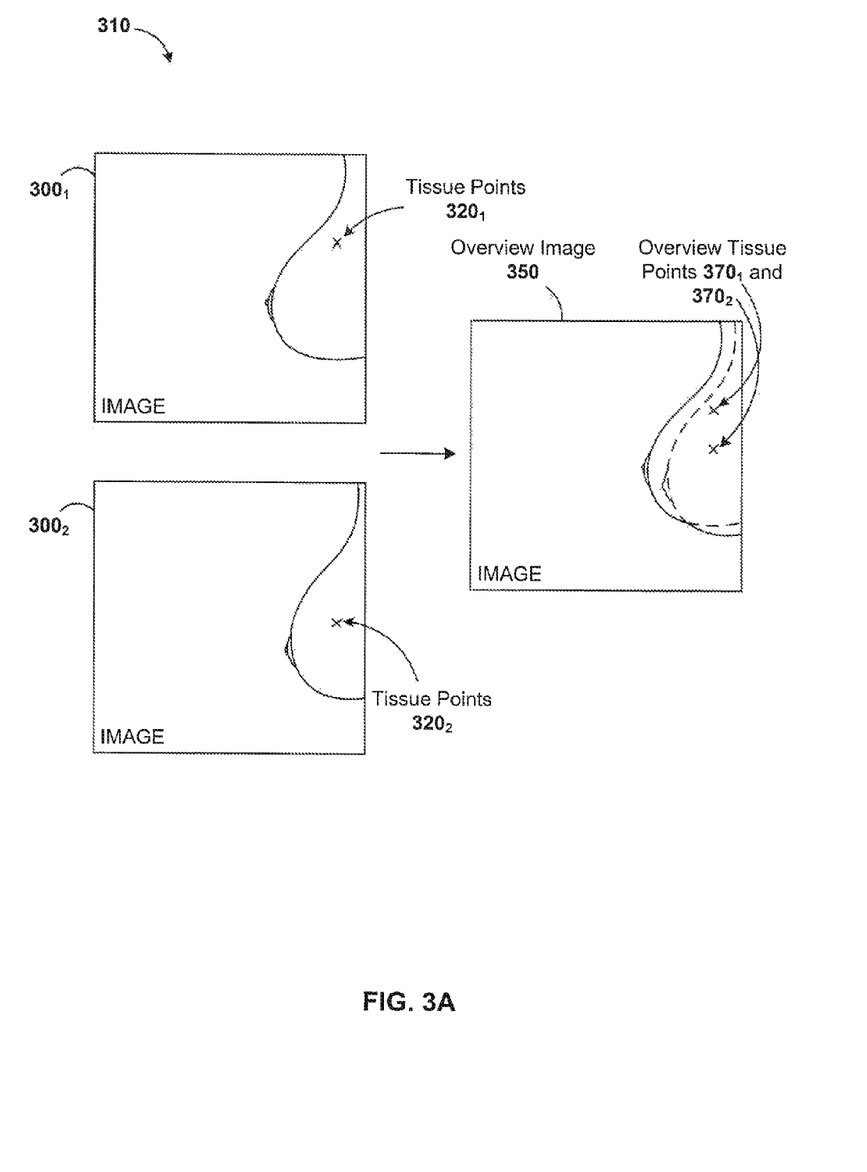
FIG. 3A is a schematic illustration of an overview image for a plurality of mammography images within the mammography system of FIG. 1A.
Figure 3B:
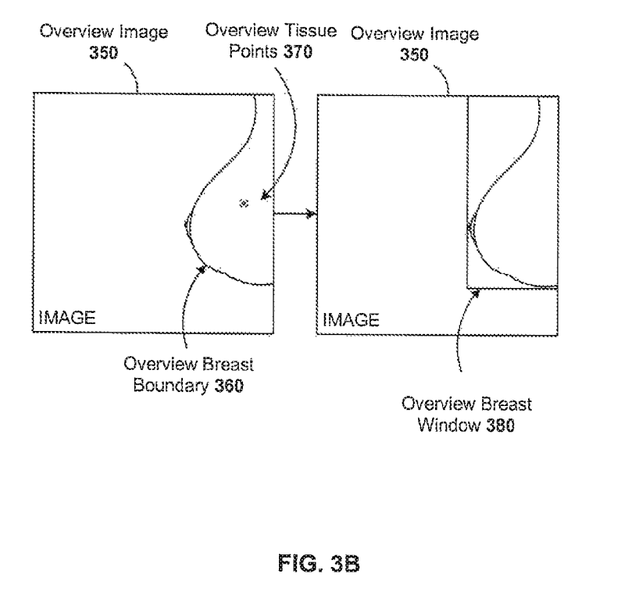
FIG. 3B is a schematic illustration of an overview breast window for an overview image within the mammography system of FIG. 1A.

Rendering module 110 may also receive notification to render an overview image 350 (FIG. 3B). The overview image 350 may be rendered based on the images of an image series 310. An overview image 350 contains overview tissue points 370 and an overview breast boundary 360 that runs along the border of the overview tissue points 370. Each overview tissue point 370 within the overview image 350 has corresponding tissue point (e.g. 320$_1$ and 320$_2$ in FIGS. 3C and 3D) in the mammography images within a given image series.

The rendering module 110 may send notifications after it has rendered a pre-scaled image 395$_n$ or an overview image 350.

Storage module 130 may be configured to receive notifications to store objects. When storage module 130 receives notification that the overview breast window 380 is defined, storage module 130 may store the overview breast window 380, or the image breast window 385$_n$, in the database 140.

Storage module 130 may also store the overview breast window 380 in the database 140 as the image breast window for each image in the series.

Database 140 may store a plurality of images 300$_1$ to 300$_n$ and breast windows, for example, an overview breast window 380 or image breast windows 385$_n$, and may be implemented using any database software or persistent storage method known in the art. For example, database 140 may be implemented using Oracle®, Microsoft SQL Server® or IBM DB2® with suitably defined schemas to identify and navigate images.

In the exemplary embodiment, database 140 may be part of a Picture Archiving and Communication Systems (PACS) deployment, such as those found in a hospital.

While database 140 is illustrated as residing in the same memory as mammography system 100, it will be understood that database 140 may be stored and accessed remotely through a network connection, for example, using a Digital Imaging and Communications in Medicine (DICOM) protocol. In such case, it will be further understood that the operations of the rendering module 110, breast window module 120, and storage module 130 may be performed locally on the mammography system, remotely on the system where the database 140 resides, or on a third-party system configured to access database 140 and mammography system 100.

Referring now to FIGS. 1A, 1B, 1C, 2A and FIG. 3A to FIG. 3E, which illustrate steps of a method 200 for generating a pre-scaled image 395$_n$ for at least one mammography image 300$_n$ of an image series 310. The pre-scaled image may be generated based on images obtained from two dimensional images, or volume-based images.

Figure 2A:
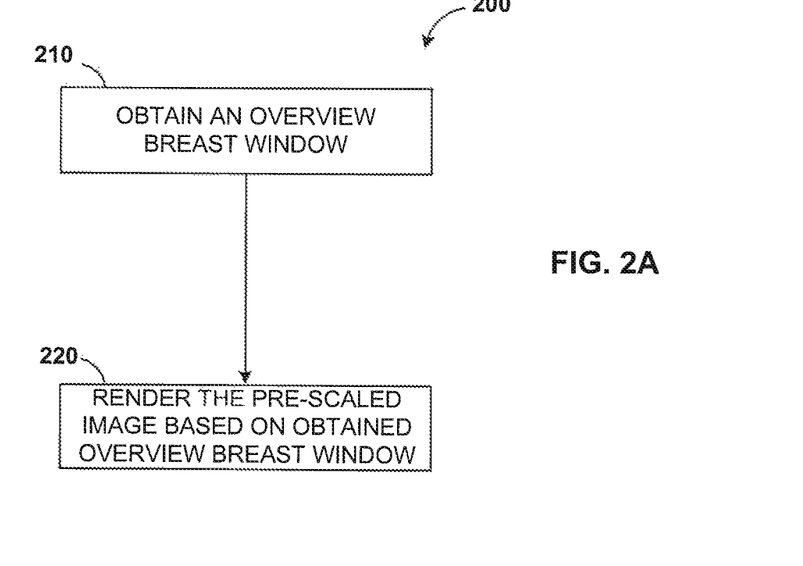
FIG. 2A is a flowchart diagram illustrating the steps of a method for generating a pre-scaled image within the mammography system of FIG. 1A.

Initially, at step (210), the image series 310 is identified and an overview breast window 380 associated with the image series 310 is obtained. After receiving notification that the overview breast window 380 has been obtained, the rendering module 110 at step (220) may render the pre-scaled image 390$_n$ using the overview breast window 380.

Referring now to FIGS. 1A, 1B, 10, 2B and FIG. 3A to FIG. 3D which illustrate steps of a method 210 for obtaining an overview breast window 380.

Figure 2B:
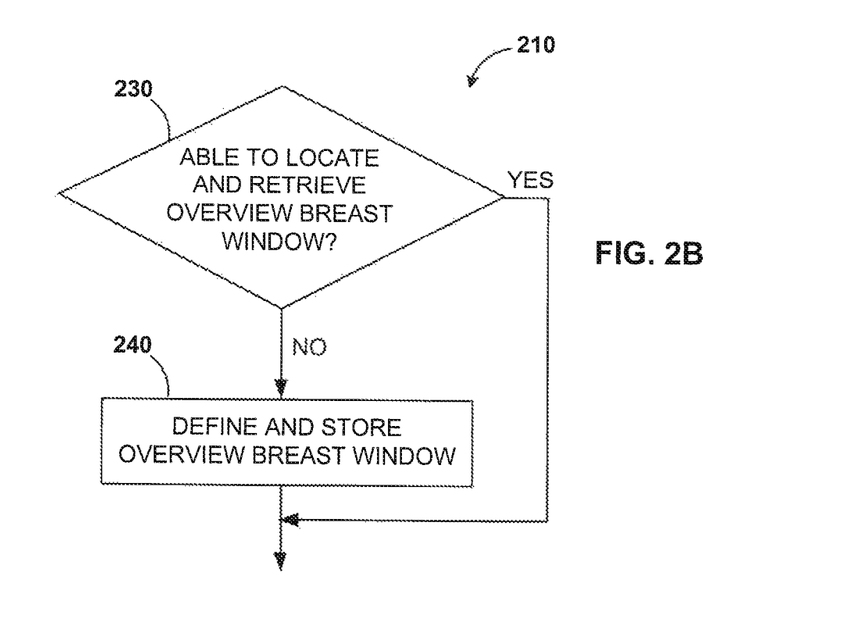
FIG. 2B is a flowchart diagram illustrating the steps of a method for obtaining an overview breast window within the mammography system of FIG. 1A.

At step (230), the overview breast window 380 may be located and retrieved from the database memory 140. If not, then at step (240) the breast window module 120 may define an overview breast window 380 and the storage module 130 may store the overview breast window 380 in the database memory. The overview breast window 380 may have been defined in the process of viewing another image of the same series.

Referring now to FIGS. 1A, 1B, 10, 20 and FIG. 3A to FIG. 3D which illustrate steps of a method 240 for defining and storing an overview breast window 380, and defining an image breast window 385$_n$ and breast window image 390$_n$. At step (250), an overview image 350 associated with the image series 310 may initially be obtained. After receiving notification that the overview image 350 is obtained, the breast window module 120 may define an overview breast window 380 at step (260) for the overview image 350.

Figure 2C:
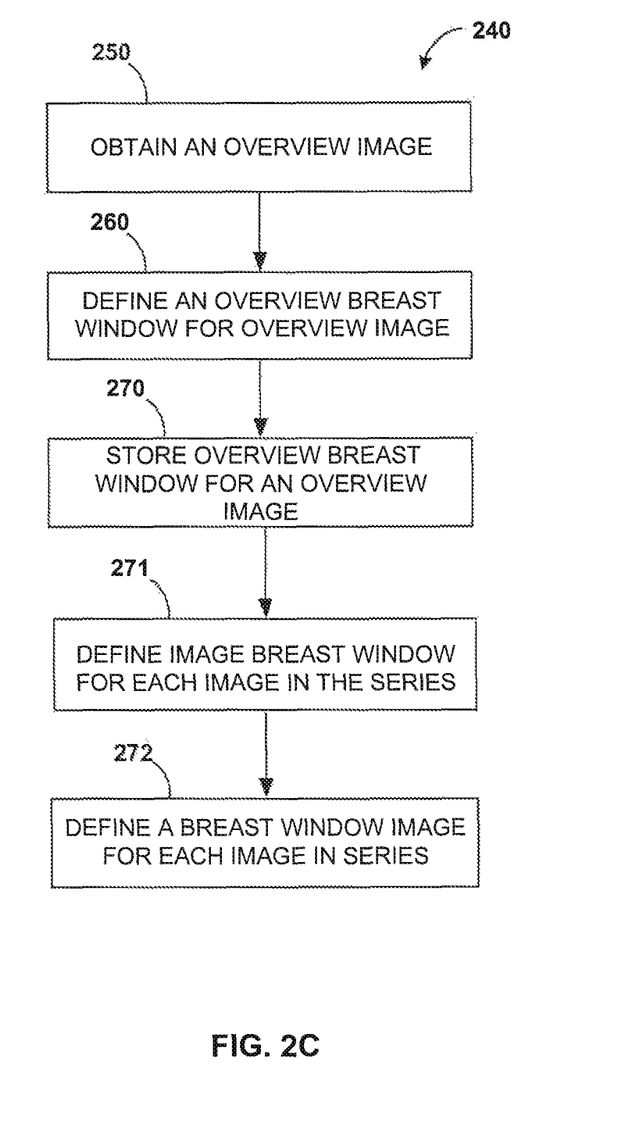
FIG. 2C is a flowchart diagram illustrating the steps of a method for defining and storing an overview breast window and defining breast window images within the mammography system of FIG. 1A.

At step (270), the overview breast window 380 may be stored in the database memory 140. In some embodiments, the overview breast window 380 may be stored in the database memory 140 as the breast window associated with each mammography image in the image series 310.

At step (271), an image breast window 385$_{1...n}$ may be defined for each image in the image series. At step (272), a breast window image 390$_{1...n}$ may be defined for each image in the series.

Referring now to FIGS. 1A, 1B, 1C, 2D and FIG. 3A to FIG. 3D which illustrate steps of a method 250 for obtaining an overview image 350.

Figure 2D:
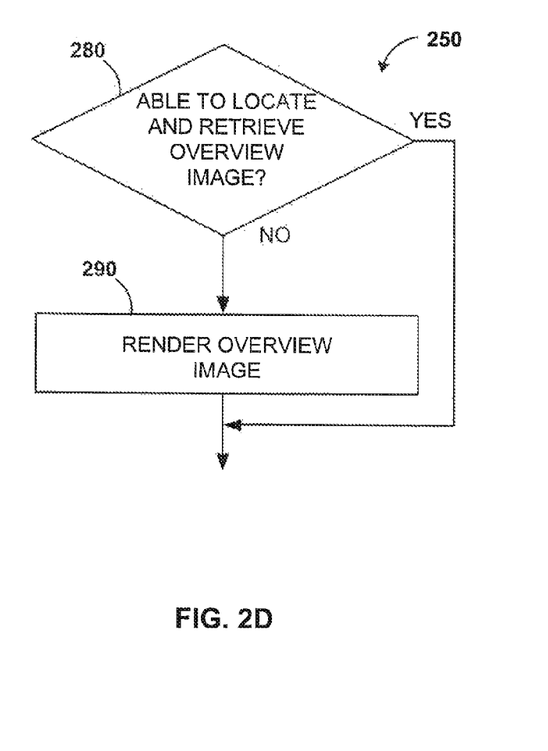
FIG. 2D is a flowchart diagram illustrating the steps of a method for obtaining an overview image within the mammography system of FIG. 1A.

At step (280), the overview image 350 may be located and retrieved from the database memory 140.

If not, then rendering module 110 at step (290) may render an overview image 350. The overview image 350 is rendered based on the images series 310. Rendering may be performed using any known method for rendering an overview image for a given plurality of mammography images (e.g. a slabbing technique).

After the overview image 350 is rendered at step (290), the rendering module 110 may send notification to the breast window module 120 that an overview image 350 is ready for breast window definition at step (260). In some embodiments, the storage module 130 may store the overview image 350 in the image database 140.

Now referring to FIG. 1A, 1B, 1C, 2E and FIG. 3A to FIG. 3D which illustrates the steps of method 271 for defining and storing an image breast window 390$_{1...n}$ for each image, 300$_{1...n}$, in an image series 310.

Figure 2E:
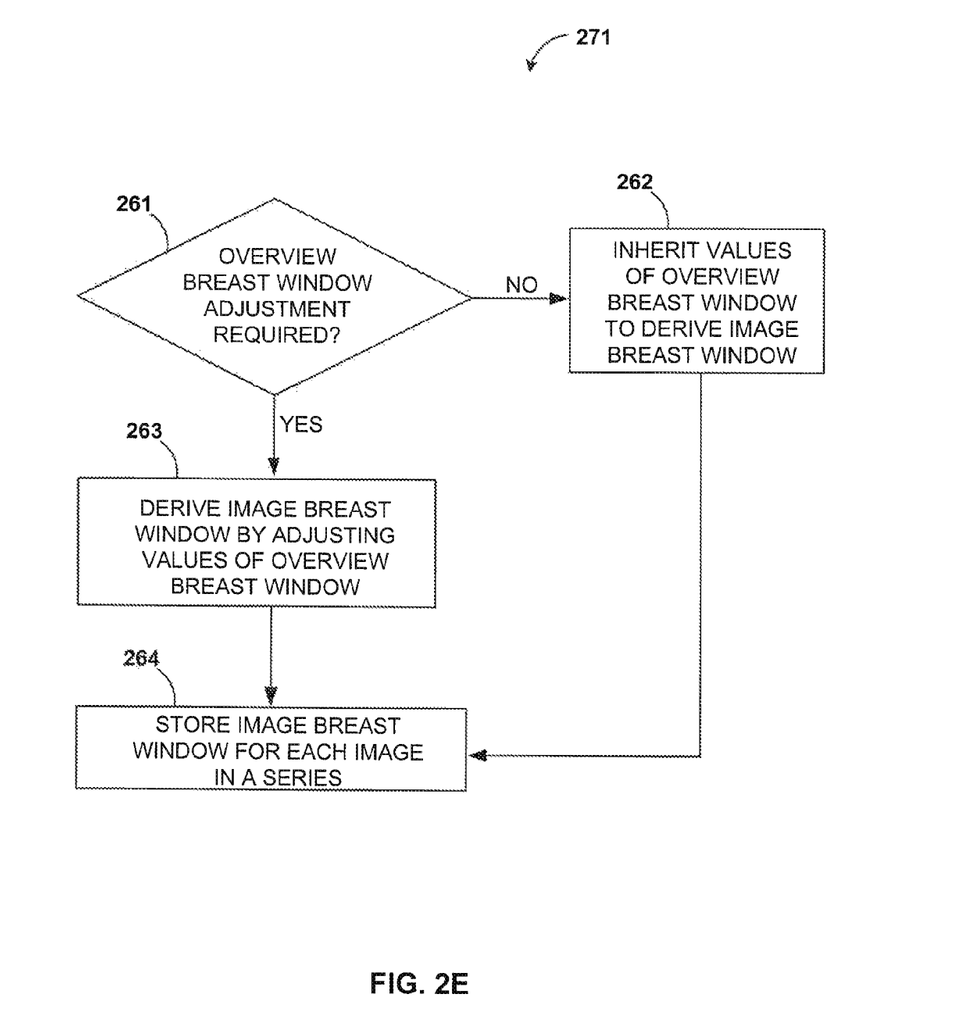
FIG. 2E is a flowchart diagram illustrating the steps for a method of defining an image breast window for at least one mammography image of a series within the mammography system of FIG. 1A.

At step (261), for each image in the series 310, the breast window module 120 checks if overview breast window requires adjustment, for example, to scale or position, and it is adjusted at step (263) if adjustment is required. Once adjusted, the image breast window 385$_n$ is derived based on the adjusted values of the overview breast window 380. The definition of the overview breast window 380 for the overview image 350 may be performed using any known method for defining a breast window for a breast image. If no adjustment is required, the values of the overview breast window are inherited to derive the image breast window 385$_n$ at step (262).

At step (264), the image breast window 385 is stored for each image in an image series 310. When the breast window definition at step (261) is complete, the breast window module 120 may send the overview breast window 380 to the storage module 130.

Now referring to FIGS. 1A, 1B and 3A, and specifically FIG. 3A which illustrates a schematic diagram of an exemplary series of mammography images 310, where the image series 310 comprise mammography images 300$_1$ and 300$_2$ stored on image database 140.

Each of the mammography images contains tissue points $320_1$ and $320_2$. Rendering module 110 (at step (290) of FIG. 2D) generates an overview image 350 based on mammography images $300_1$ and $300_2$ wherein each mammography image tissue point $320_1$ and $320_2$ of mammography images $300_1$ and $300_2$ is represented by an overview tissue points $370_1$ and $370_2$ in the overview image 350. The overview image 350 may be stored on image database 140.

Referring to FIGS. 1A, 1B, 2O, 3A and 3B, and specifically FIG. 3B which illustrates a schematic diagram of an overview image 350 stored on image database 140. The overview image 350 comprises an overview tissue point 370 and an overview breast boundary 360 formed along the border of the overview tissue point.

The breast window module 120 (at step (260) of FIG. 2O) defines an overview breast window 380 by identifying the smallest region (e.g. a rectangle in one embodiment) that encloses all (as it is defined by an algorithm used) of the overview tissue point 370.

Figure 3C:
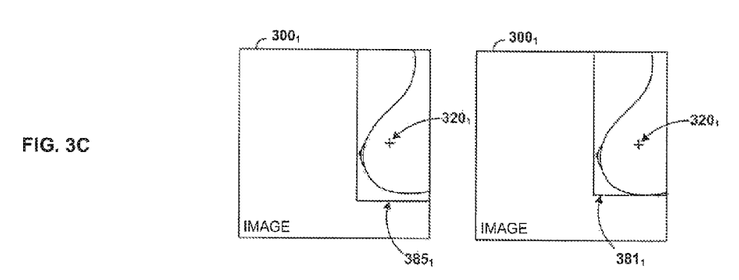
FIG. 3C is a schematic illustration of an overview breast window for a mammography image compared to an image breast window defined for the individual mammography image within the mammography system of FIG. 1A.
Figure 3D:
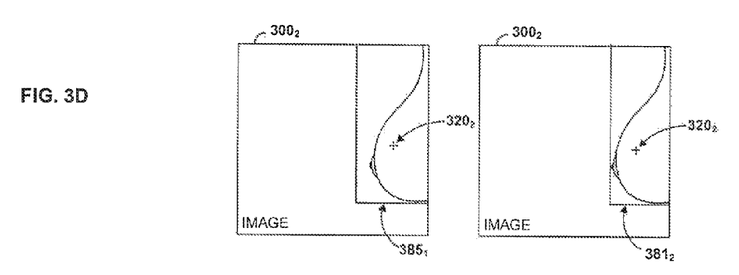
FIG. 3D is a schematic illustration of an overview breast window for a mammography image compared to an image breast window defined for the individual mammography image within the mammography system of FIG. 1A; and, FIG. 3E is a schematic illustration of a pre-scaled image for a mammography image of an image series within the mammography system of FIG. 1A.
Figure 3E:
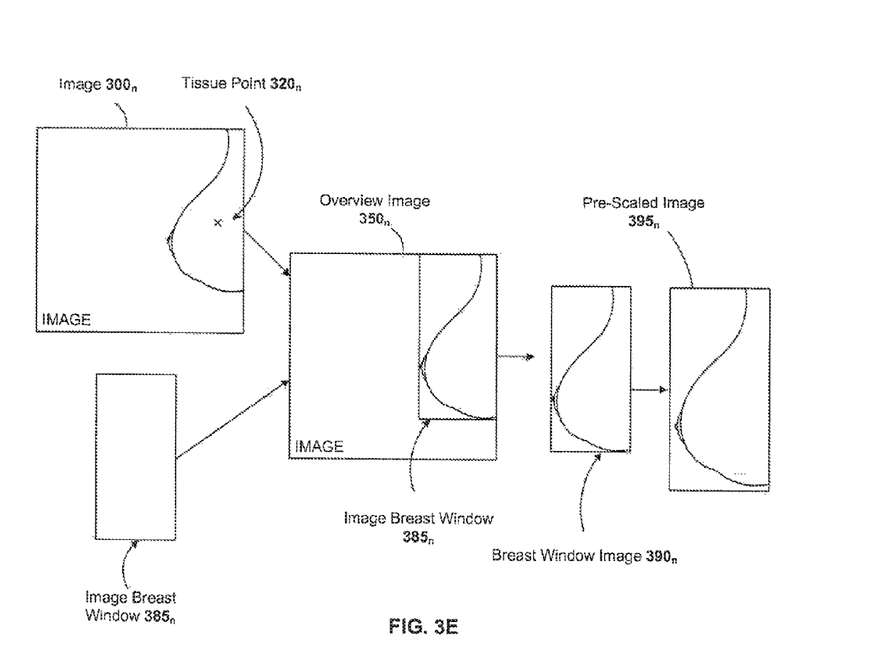

Referring to FIGS. 1A, 1B, 2O, 3B, and 3E, and specifically FIG. 3E which illustrates a schematic diagram of a pre-scaled image $395_n$, for an image $300_n$ from image series 310. The image $300_n$ is stored on image database 140 along with the corresponding image breast window $385_n$. The breast window module 120 (at step (260) of FIG. 2C) defines the image breast window $385_n$ by adjusting, if necessary, the overview breast window 380.

Referring to FIGS. 1A, 1B, 3C and 3D, and specifically FIG. 3D which illustrates a schematic diagram of the image breast window $385_1$ for the mammography images $300_1$ and $300_2$ of FIG. 3A.

The storage module 130 (at step (270) of FIG. 2C) stores the overview breast window 380 for the images series 310. As can be seen, the overview breast window 380 is an approximation of the smallest region that encloses all of the tissue points $320_1$ and $320_2$ on the images $300_1$ and $300_2$.

It is worthwhile noting that if the breast window definition had been performed using the individual mammography image $300_1$ instead of the overview image 350, the smallest region (e.g. rectangle in one embodiment) that encloses all of the tissue points $320_1$ in mammography image $300_1$ would be identified by the region $381_1$ of FIG. 3O.

Likewise, if the breast window definition had been performed on the individual mammography image $300_2$ instead of the overview image 350, the smallest region that encloses all the tissue points $320_2$ in mammography image $300_2$ would be identified by the region $381_2$ of FIG. 3D.

Without the overview breast window definition disclosed by the present invention, the system would perform image processing on every image $300_1$ to $300_n$ in order to determine the breast window $381_1$ and subsequently allow pre-scaled view image $300_2$ with the breast window $381_2$.

The method disclosed in the present invention of generating a pre-scaled image is not limited to two-dimensional images and may be used to generate a pre-scaled image as well.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto.

The invention claimed is:

1. A computer-implemented method for generating a pre-scaled image displayed within a viewing area of a mammography system for at least one mammography image of a series, the series containing a plurality of mammography images, each mammography image displaying a breast image having tissue points, the method comprising:
   determining, by a processor, if an overview breast window for the series is stored in a database memory coupled to the processor, wherein the overview breast window is the smallest region that encloses all the tissue points of each mammography image of the series;
   if so, locating and retrieving, from the database memory, the overview breast window; and
   otherwise, defining and storing, in the database memory, the overview breast window; and
   rendering, by the processor, the pre-scaled image based on the overview breast window.

2. The method of claim 1, wherein the overview breast window is defined and stored by:
   the processor obtaining an overview image for the series, wherein the overview image includes overview tissue points that each correspond to one of the tissue points within the mammography images of the series;
   the processor defining the overview breast window for the overview image as the smallest region that encloses each of the overview tissue points; and,
   storing the overview breast window for the overview image in the database memory.

3. The method of claim 2, wherein obtaining the overview image comprises the processor determining, from the database memory, if the overview image is stored in the database memory;
   if so, locating and retrieving, from the database memory, the overview image; and
   otherwise, rendering the overview image.

4. The method of claim 3, wherein the processor renders the overview image based on the volume based series of mammography images.

5. The method of claim 3, further comprising storing the overview image in the database memory.

6. The method of claim 2, wherein the processor defines the overview breast window for the overview image to include:
   a size of a smallest region that encloses the overview tissue points; and,
   a location of the smallest region within the overview image.

7. The method of claim 1, further comprising:
   the processor defining an image breast window for each mammography image of the series based on the overview breast window;
   the processor determining if the mammography images in the series are aligned;
   if the mammography images in the series are aligned, storing the overview breast window as the image breast window for each mammography image of the series; and
   otherwise, adjusting, by the processor, the overview breast window and storing the adjusted overview breast window as the image breast window for each mammography image of the series.

8. The method of claim 1 wherein rendering the pre-scaled image comprises the processor mapping the pre-scaled image to the viewing area of the mammography system.

9. A non-transitory computer-readable storage medium comprising a plurality of instructions for execution on a processor, the instructions for performing the steps of the method of claim 1.

10. A system for generating a pre-scaled image displayed within a viewing area of a mammography system for at least one mammography image of a series, the series containing a plurality of mammography images, each mammography image displaying a breast having tissue points, the system comprising:
 a database memory for storing an overview breast window;
 a processor coupled to the database memory; and
 a non-transitory computer-readable storage medium storing instructions for configuring the processor to:
  determine if an overview breast window for the series is stored in the database memory, wherein the overview breast window is the smallest region that encloses all the tissue points of each mammography image of the series;
  if so, locate and retrieve the overview breast window from the database memory; and
  otherwise, define and store the overview breast window in the database memory; and
 render the pre-scaled image based on the overview breast window.

11. The system of claim 10, wherein the storage medium further stores instructions for configuring the processor to:
 obtain an overview image for the series, wherein the overview image includes overview tissue points that each correspond to one of the tissue points within the mammography images of the series;
 define the overview breast window for the overview image as the smallest region that encloses each of the overview tissue points; and,
 store the overview breast window for the overview image in the database memory.

12. The system of claim 11, wherein the storage medium further stores instructions for configuring the processor to:
 determine if the overview image is stored in the database memory; and
 if so, locate and retrieve the overview image from the database memory; and
 otherwise, render the overview image.

13. The system of claim 12, wherein the overview image is rendered based on the mammography images of the series.

14. The system of claim 12, wherein the storage medium further stores instructions for configuring the processor to define the overview breast window for the overview image by a size of a smallest region that encloses the overview tissue points and a location of the smallest region within the overview image.

15. The system of claim 10, wherein the storage medium further stores instructions for configuring the processor to define an image breast window for one of the mammography images by
 determining if the overview breast window requires adjustment;
 adjusting the overview breast window; and
 storing the adjusted overview breast window as the image breast window.

16. The system of claim 10 wherein rendering the pre-scaled image comprises mapping the pre-scaled image to the viewing area of the mammography system.

* * * * *